United States Patent [19]

Vincent et al.

[11] Patent Number: 5,194,246
[45] Date of Patent: Mar. 16, 1993

[54] ANTICALCULUS ORAL COMPOSITIONS CONTAINING COMBINATIONS OF POLYMERS

[75] Inventors: Carol K. Vincent, Wanaque; David L. Elliott, Hawthorne; Catherine L. Howie-Meyers, Bloomingdale, all of N.J.

[73] Assignee: Chesebrough-Pond's USA Co., Division of Conopco, Inc., Greenwich, Conn.

[21] Appl. No.: 686,106

[22] Filed: Apr. 16, 1991

[51] Int. Cl.$^5$ .............................. A61K 7/16
[52] U.S. Cl. ........................ 424/57; 424/78.11
[58] Field of Search ............. 424/59, 60, 57, 78.11

[56] References Cited

U.S. PATENT DOCUMENTS

| | | | |
|---|---|---|---|
| 2,380,473 | 4/1942 | Stewart et al. | 526/233 |
| 3,429,963 | 2/1969 | Shedlovsky | 424/56 |
| 3,934,002 | 1/1976 | Haefele | 424/49 |
| 4,183,914 | 1/1980 | Gaffar et al. | 424/58 |
| 4,515,772 | 5/1985 | Parran, Jr. et al. | 424/49 |
| 4,590,066 | 5/1986 | Parran, Jr. et al. | 424/57 |
| 4,627,977 | 12/1986 | Gaffar et al. | 424/49 |
| 4,661,341 | 4/1987 | Benedict et al. | 424/48 |
| 4,681,686 | 7/1987 | Richardson et al. | 526/233 |
| 4,684,518 | 8/1987 | Parran, Jr. et al. | 424/52 |
| 4,806,340 | 2/1989 | Gaffar et al. | 424/49 |
| 4,806,342 | 2/1989 | Gaffar et al. | 424/49 |
| 4,808,400 | 2/1989 | Gaffar et al. | 424/57 |
| 4,842,847 | 6/1989 | Amjad | 424/57 |
| 4,847,070 | 7/1989 | Pyrz et al. | 424/52 |
| 4,892,724 | 1/1990 | Amjad | 424/49 |
| 4,892,725 | 1/1990 | Amjad | 424/49 |
| 5,011,682 | 4/1991 | Elliott et al. | 424/52 |

FOREIGN PATENT DOCUMENTS 2-34694  2/1990  Japan .................. 526/233

*Primary Examiner*—Thurman K. Page
*Assistant Examiner*—Peter F. Kulkosky
*Attorney, Agent, or Firm*—Milton L. Honig, Esq.

[57] ABSTRACT

A method and composition for controlling calculus formation in the mouth is reported based upon a combination of a low and high molecular weight polymer. The first polymer is a synthetic anionic polymer having a molecular weight of at least 4000. The second polymer has a molecular weight up to about 2500 and is formed from a mixture of mono- and di- carboxylic vinyl monomers reacted with hypophosphite groups.

19 Claims, No Drawings

ANTICALCULUS ORAL COMPOSITIONS CONTAINING COMBINATIONS OF POLYMERS

BACKGROUND OF THE INVENTION

1. Field of the Invention

The invention relates to new anticalculus agents, dentifrice compositions containing these agents and use of these compositions to control calculus accumulation on teeth.

2. Related Art

Calculus is a hard, mineralized deposit which forms around teeth. This formation arises from deposition of crystals of calcium phosphate in the pellicle and the extracellular matrix of dental plaque. Various forms of calcium phosphate have been identified but the most difficult to remove and thermodynamically most stable form is called hydroxyapatite (HAP). Amorphous forms of calcium phosphate are believed to be the precursors of HAP. Regular brushing can usually remove the amorphous forms but is not fully effective to dislodge the final stable calculus form. Therefore it is desirable to prevent amorphous forms of calcium phosphate from transforming into HAP. The art has recognized that agents which interfere with the formation of HAP crystallization will be effective anticalculus agents.

Soluble inorganic pyrophosphate salts have over the last few years set the commercial standard as calculus or tartar control agents. This technology has been reported by Parran, Jr. et al. in a series of patents including U.S. Pat. No. 4,590,066, U.S. Pat. No. 4,515,772 and U.S. Pat. No. 4,684,518.

Anionic polymers, especially carboxylate group functionalized polymers, have been widely reported as effective against calculus. Typically, low molecular weight anionic materials of high charge density are preferred in most of the prior art. For example, U.S. Pat. No. 4,661,341 (Benedict et al.) discloses the use of low molecular weight polyacrylic acids (MW range 3500 to 7500) in dental compositions. U.S. Pat. No. 3,429,963 (Shedlovsky) teaches use of maleate-containing copolymers and vinyl sulfonates in toothpaste. U.S. Pat. No. 4,183,914 (Gaffar et al.) reports use of polymaleates as anticalculus agents. The materials of Gaffar et al. cannot be obtained above molecular weight 1,000 and often have low purity in available commercial samples. High levels of impurities result in polymeric materials of poor appearance, taste and inadequate safety.

Commercially most significant has been the use of synthetic, linear anionic polymers of higher molecular weight in combination with the inorganic pyrophosphates. This technology derives from work done by Gaffar et al. reported in a series of patents including U.S. Pat. No. 4,627,977, U.S. Pat. No. 4,806,340, U.S. Pat. No. 4,806,342, U.S. Pat. No. 4,808,400 and U.S. Pat. No. 4,808,401. Anionic polymers described therein were found to inhibit the action of pyrophosphatases in the mouth and thereby allow greater efficacy of the inorganic pyrophosphate. The commercially operative polymer is a methyl vinyl ether/maleic anhydride copolymer, available under the GAF trademark Gantrez.

Organic phosphonic acid derivatives, some in polymeric form, have been disclosed in U.S. Pat. No. 3,934,002 (Haefele). U.S. Pat. No. 4,892,724 (Amjad) cites a tartar inhibiting oral composition that includes a fluoride source, a dental abrasive, a carboxylate polymer and various phosphonic acids and their derivatives. A phosphated acrylic acid/hydroxyethyl methacrylate-/alkyl methacrylic acid ester copolymer has been suggested in GB 2 139 635B (Causton) as useful in an oral composition for treating teeth. U.S. Pat. No. 4,892,725 (Amjad) reports a fluoride oral composition with an anticalculus agent that includes a first polymer selected from homopolymers of carboxyl monomers and a second polymer which is a copolymer containing at least 30% of the carboxyl monomer. Related to this disclosure is U.S. Pat. No. 4,842,847 (Amjad) focusing upon a fluoride containing oral composition having an anticalculus agent selected from homo and copolymers, the latter containing at least 30% by weight of monocarboxylic or dicarboxylic monomer units. Combinations of polyacrylic acid derivatives, strontium and fluoride ion sources along with a soluble pyrophosphate have been reported in U.S. Pat. No. 4,847,070 (Pyrz et al.).

Evident from the foregoing review of the art is the considerable effort expended to devise better calculus control compositions. By no means, however, has any of the reported art been able to more than attenuate the problem. There is considerable room for improvement over the known control agents.

Accordingly, it is an object of the present invention to provide a material of improved efficacy in controlling formation of calculus.

A still further object of the present invention is to provide a tartar control agent of improved taste, safety and appearance.

These and other objects of the present invention will become more apparent in light of the detailed description and Examples which follow.

SUMMARY OF THE INVENTION

An oral composition is provided comprising:

(i) a synthetic anionic polymer having a molecular weight greater than about 4000;

(ii) a polymer having the formula I:

wherein A is a random polymeric residue comprising at least one unit of structure II,

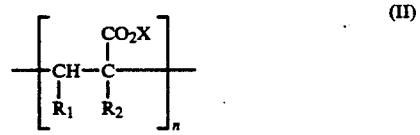

and at least one unit of structure III, different from a unit of structure II,

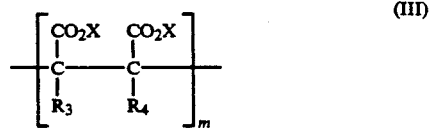

and B is hydrogen or a residue A; m and n are integers sufficient to provide polymer of weight averaged molecular weight ranging from about 400 to about 2500; m and n in residue A may each be the same or different from respective m and n in residue B; R is an —OX, where X is selected from the group consisting of hydrogen, alkali metal, alkaline earth metal, transition metal, ammonium, alkyl amine, alkanolammonium residues and mixtures thereof; $R_1$, $R_2$, $R_3$ and $R_4$ are hydrogen, methyl, ethyl radicals or combinations thereof, and the synthetic anionic polycarboxylic polymer relative to polymer I being present in a weight ratio from about 10:1 to about 1:10.

DETAILED DESCRIPTION

Now it has been discovered that anticalculus activity can substantially be improved by employing a combination of polymers, the first having a molecular weight greater than about 4000 and the second having a molecular weight of between about 400 to 2500.

A wide variety of synthetic anionic polymers, especially polycarboxylate polymers, may be employed as the high molecular weight (4000 and above) material. More specifically, the high molecular weight polymer is a homo or copolymer formed from monomers comprising mono-unsaturated mono-carboxylic and di-carboxylic acids having 3 to 5 carbon atoms, salts, esters and anhydrides thereof, and which have at least one activated olefinic double bond. The high molecular weight polycarboxylate polymer may be a phosphorus- or non-phosphorus-containing material.

Illustrative monomers useful for forming the first synthetic anionic high molecular weight polymer are carboxylic acids such as acrylic, methacrylic, ethacrylic, alpha-chloroacrylic, crotonic, beta-acryloxy propionic, sorbic, alpha-chlorosorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides thereof. The preferred carboxylic acids are acrylic acid, methacrylic acid, itaconic acid, maleic acid and its anhydride, citraconic acid, and mesaconic acid. Acrylic, methacrylic, maleic, and itaconic acids are especially preferred. Comonomers which can be copolymerized with one or more of the carboxyl monomers include acrylamides, alkyl acrylates, alkyl itaconates, vinylsulfonic acid, hydroxyalkyl acrylates, alkoxyalkyl acrylates, lower alkenyl carboxylates, styrenesulfonic acids, allyloxyhydroxyalkane sulfonic acids, acrylamidoalkane sulfonic acids, sulfoloweralkyl acrylates, polymerized vinyl alcohols, anhydrides and salts thereof.

Suitable acrylamide monomers are defined as follows:

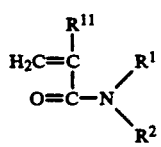

where $R^{11}$ is hydrogen or methyl and $R^1$ and $R^2$ are individually selected from hydrogen, alkyl and substituted alkyl groups each containing a total of 1 to 12, preferably 1 to 8 carbons. Preferred acrylamides are the substituted acrylamides where either $R^1$ or $R^2$ is not hydrogen. Substituents on the alkyl groups include alkyl, aryl, hydroxyl, hydroxyalkyl, carboxylic acid, and keto groups. Specific examples of substituted acrylamides include, t-butyl acrylamide, isopropyl acrylamide, isobutyl acrylamide, methyl acrylamide, t-butyl methacrylamide, 2-(2,4,4-trimethyl pentyl) acrylamide, 2-(2-methyl-4-oxopentyl) acrylamide, hydroxymethyl acrylamide, hydroxypropyl acrylamide, diacetone acrylamide, and 3-acrylamido-3-methylbutanoic acid.

Suitable alkyl acrylate monomers are defined as follows:

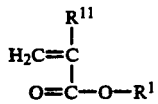

where $R^{11}$ is hydrogen or methyl and $R^1$ is selected from alkyl groups of 1 to 6 carbons and substituted alkyl groups where $R^1$ is defined as $R^2$—Y, where $R^2$ is an alkyl group containing from 1 to 6 carbon atoms and Y is —$SO_3X$, —$C(O)R^1$ or —$CO_2X$ where X is hydrogen, alkali metal, alkaline earth metal, or ammonium, and $R^3$ is alkyl of 1 to 3 carbon atoms. In a preferred embodiment, the $R^1$ group is unsubstituted and has 1 to 4 carbon atoms. Specific examples of suitable monomeric alkyl acrylates and methacrylates include ethyl acrylate, ethyl methacrylate, sulfopropyl acrylate, and carboxyethyl acrylate.

Suitable alkyl itaconate monomers have the following structure:

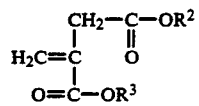

where $R^2$ and $R^3$ are individually selected from hydrogen, alkyl and substituted alkyl groups of 1 to 12 carbon atoms in the alkyl group, provided that both $R^2$ and $R^3$ are not hydrogen although either $R^2$ or $R^3$ can be hydrogen. Substituents on the $R^2$ and $R^3$ groups include lower alkyl, aryl such as phenyl, and keto groups, however in a preferred embodiment, $R^2$ and $R^3$ are individually selected from unsubstituted lower alkyl groups of 1 to 4 carbon atoms. Specific examples of preferred $R^2$ and $R^3$ groups include methyl, ethyl, propyl, isopropyl, butyl and isomeric forms thereof, and the like. Preferred herein are the diesters of itaconic acid. Specific examples of preferred itaconic acid esters include dimethyl itaconates, diethyl itaconates and dibutyl itaconate.

Suitable vinylsulfonic acid and salts thereof which can be monomers are defined as follows:

where X is selected from hydrogen, alkali metal, alkaline earth metal, and an ammonium groups, preferably and alkali metal and ammonium groups. Preferred vinylsulfonic acid salt is sodium vinylsulfonate where X in the above formula is sodium.

Suitable hydroxyalkyl acrylate monomers are defined as follows:

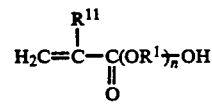

where $R^{11}$ is hydrogen or a lower alkyl of 1 to 3 carbon atoms, preferably hydrogen or methyl; $R^1$ is selected from lower alkylene groups of 2 to 4, preferably 2 to 3 carbon atoms; and n is an integer from 1 to 5. Some specific examples of suitable hydroxyalkyl acrylates include hydroxypropyl acrylate and hydroxypropyl methacrylate.

Suitable alkoxyalkyl acrylate monomers are defined as follows:

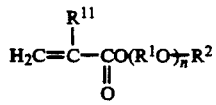

where R is hydrogen or methyl, $R^1$ is an alkylene group containing from 2 to 4, but preferably 2 to 3 carbon atoms, n is an integer from 1 to 5 but preferably 1 to 3, and $R^2$ is an alkyl group containing from 1 to 10 preferably 1 to 4 carbon atoms. Specific examples of alkoxyalkyl acrylate monomers include methoxyethyl acrylate, cellosolve methacrylate, and 2-(2-ethoxyethoxy) ethyl acrylate.

Suitable vinyl carboxylate monomers are defined as follows:

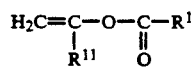

where R is hydrogen or a lower alkyl group of 1 to 6 carbon atoms, preferably hydrogen or alkyl of 1 to 2, and $R^1$ is selected from alkyl groups of 1 to 12 carbon atoms, preferably 1 to 8.

The vinyl carboxylates, in polymerized form, can be hydrolyzed to contain polymerized vinyl alcohol which has repeating units of the following structure:

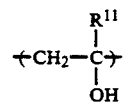

where $R^{11}$ is hydrogen or a lower alkyl group of 1 to 6 carbon atoms, preferably hydrogen or alkyl of 1 to 2. The $R^{11}$ group of the hydrolyzed carboxylates corresponds to the R group on the vinyl carboxylates. Specific examples of vinyl carboxylates include vinyl acetate, vinyl propionate and 2-propenyl acetate.

Styrenesulfonic acids and salts thereof suitable as monomers are defined as follows:

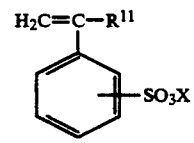

where $R^{11}$ is hydrogen or a lower alkyl group of 1 to 6 carbon atoms, but preferably hydrogen, and X is hydrogen, alkali metal or alkaline earth metal or ammonium but particularly hydrogen, ammonium or alkali metal. A particularly suitable sulfonic acid is styrenesulfonic acid where R is hydrogen and the —$SO_3$ group is at the 3 or 4 position on the phenyl ring. The salts of styrenesulfonic acids are water-soluble. The sodium salt of styrenesulfonic acid is available commercially.

Allyloxyhydroxyalkanesulfonic acids and salts thereof suitable as monomers are defined as follows:

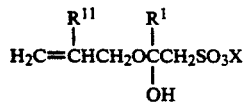

where $R^{11}$ and $R^1$ are each hydrogen or methyl, and X is selected from hydrogen, alkali metal, alkaline earth metal and ammonium groups. A preferred monomer in this group is the sodium salt of 3-allyloxy-2-hydroxypropanesulfonic acid.

Acrylamidoalkanesulfonic acids and salts thereof suitable as monomers have the general formula:

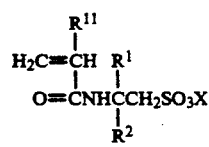

where $R^{11}$ is hydrogen or methyl; X is selected from hydrogen, ammonium, alkali metal or alkaline earth metal, particularly hydrogen, ammonium, or an alkali metal; and $R^1$ and $R^2$ are individually selected from hydrogen and alkyl groups of 1 to 4 carbon atoms In a preferred embodiment, $R^{11}$ is hydrogen and $R^1$ and $R^2$ are each an alkyl group of 1 of 3 carbon atoms. X in the above structural formula represents hydrogen or any metal cation which does not adversely affect the water solubility of the polymer, such as sodium, potassium and ammonium cations. In addition, X may also represent calcium, magnesium, and lithium, since they do not present any adverse effects on the solubility of the polymer. A particularly suitable monomer in accordance with the present invention is 2-acrylamido-2-methylpropanesulfonic acid.

Suitable sulfoalkyl acrylate monomers have the following structure:

where $R^{11}$ is selected from hydrogen, methyl and the group —$CH_2C(O)OR^2SO_3X$ where $R^2$ is selected from alkylene groups of 1 to 2 carbons, preferably 2 to 4 carbons; and where X is selected from hydrogen, alkali metals, alkaline earth metals, and ammonium but particularly hydrogen, sodium, potassium, calcium, magnesium, and ammonium. The sulfo group —$SO_3X$, is preferably located on the last carbon atom of the $R^2$ group. The $R^2$ group can be substituted or unsubstituted. Substituents on $R^2$ group are selected from those which do not adversely affect the anticalculus activity of the polymer. Preferred sulfoalkyl acrylates include 2-sulfoethyl methacrylate, 3-sulfopropyl acrylate, 3-sulfopropyl methacrylate and bis-(3-sulfopropyl) itaconate.

The above monomers can be prepared, if desired, in any conventional manner but they are also commercially available. Polymerization of the monomers preferably results in essentially non-crosslinked polymers, the molecular weight of which can be adjusted through known techniques.

A critical second element of the invention is a low molecular weight copolymer of, for example, acrylic acid and maleic acid (and other carboxylic monomers) whose structure is modified to include mono- or disubstituted hypophosphite units along the polymer backbone. These materials are different in structure from typical acrylate/maleate copolymers in two respects. First, as noted they contain phosphite or hypophosphite groups. Secondly, they are of unusually low molecular weight, preferably no higher than 2500. They must contain a monocarboxylic acid monomer, a dicarboxylic acid monomer, and a hypophosphite, which when reacted will form low molecular weight polymers of this invention having the general structure:

 (I)

wherein A is a random polymeric residue comprising at least one unit of structure II,

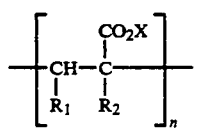 (II)

and at least one unit of structure III, different from a unit of structure II,

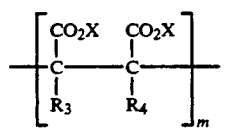 (III)

and B is hydrogen or a residue A; m and n are integers sufficient to provide polymer of weight averaged molecular weight ranging from about 400 to about 2500; m and n in residue A may each be the same or different from respective m and n in residue B; R is an —OX, where X is selected from the group consisting of hydrogen, alkali metal, alkaline earth metal, transition metal, ammonium, alkyl amine, alkanolammonium residues and mixtures thereof; $R_1$, $R_2$, $R_3$ and $R_4$ are hydrogen, methyl, ethyl radicals or combinations thereof.

Polymers forming the structure II will have a single carboxylic acid or salt group. There will be anywhere from 3 to 7 carbon atoms for this structure. Suitable monomers include acrylic acid, methacrylic acid, alpha-substituted alkyl acrylic acids, and beta-carboxyalkyl acrylates.

Monomers that form structure III will have at least two carboxylic acid groups and may range from 4 to 7 carbon atoms in size. Suitable monomers include maleic acid, fumaric acid, itaconic acid, mesaconic acid, citraconic acid, their anhydrides or salts.

Specific salts of the mono- and di- carboxylic monomers may be those including the counterions of sodium, potassium, calcium, strontium, zinc, copper, ammonium, $C_2$-$C_9$ alkanolammonium, $C_1$-$C_8$ alkyl amine and mixtures thereof. Sodium, strontium and zinc are particularly preferred counterions.

Most preferred are copolymers formed from acrylic acid and maleic acid.

Polymers of Formula I are telomeric. Sodium hypophosphite is present in the polymerization medium to control molecular weight and to be incorporated into the backbone as mono- or disubstituted hypophosphite groups. These groups may be incorporated at the chain end or between monomer units in the chain. Typically, 70-90% of the total hypophosphite groups will be disubstituted. These groups are essential for the enhanced benefit of the polymers of this invention.

Molar ratio of total monomer to hypophosphite of the raw components before polymerization may range from about 40:1 to about 1:1, preferably from about 20:1 to about 4:1, optimally between about 16:1 to about 7:1. Lower ratios of monomer to hypophosphite generally result in lower polymer molecular weight and higher levels of incorporation of hypophosphite in the polymers.

Dicarboxylic monomers should be present in amounts in the copolymer ranging from about 10 to about 95 mole percent, preferably from about 20 to about 75 mole percent. Molar ratios of monocarboxylic monomer to dicarboxylic monomer should preferably be from about 5:1 to about 1:5, optimally between about 4:1 to about 1:1.

Typically, both the high (synthetic anionic) and low (hypophosphite) molecular weight polymers will be used at ratios of about 10:1 to about 1:10, preferably about 6:1 to 1:6. About 0.1 to 10% of the combination of the two polymers will normally be employed in the oral compositions of this invention, more preferably from about 0.4 to about 7%, optimally between about 1 to about 5% by weight.

The synthetic anionic polymer as noted has a molecular weight of at least 4,000 and may be as high as about 1,000,000, with about 4,000 to about 700,000 being preferred. The other polymer may have a molecular weight ranging from about 600 to less than 2,500, preferably between 1,000 to 2,300.

Carriers suitable for use with the polymers are preferably hydroxylic materials such as water, polyols and mixtures thereof. Polyols, sometimes referred to as humectants, include glycerol, sorbitol, propylene glycol, lactitol, xylitol, polypropylene glycol, polyethylene glycol, hydrogenated corn syrup and mixtures thereof. Particularly preferred as the carrier is a liquid mixture of 3-30% water, 0-80% glycerol and 20-80% sorbitol. Generally the amount of carrier will range from about 25 to 99.9% by weight, preferably from about 70 to 95% by weight.

When the compositions of this invention are in the form of a toothpaste or gel there will typically be included a natural or synthetic thickening agent in an amount from 0.1-10%, preferably about 0.5-5% by weight. Thickeners may include hydroxypropyl methyl cellulose, hydroxyethyl cellulose, sodium carboxymethyl cellulose, xanthan gum, tragacanth gum, karaya gum, arabic gum, Irish moss, starch, alginates and carrageenans. The amount of thickening agent will generally be between about 0.1 and 10% by weight.

Surfactants are normally also included in the oral compositions of this invention. These surfactants may be of the anionic, nonionic, cationic or amphoteric type. Most preferred are sodium lauryl sulfate, sodium dodecylbenzene sulfonate and sodium laurylsarcosinate. Surfactants are usually present in an amount from about 0.5 to 5% by weight.

When in the form of a toothpaste or gel, the oral compositions will normally include an abrasive. Abrasives may be selected from water-insoluble alkali or alkaline earth metal salts of metaphosphate, calcium carbonate, aluminates and silicates. Especially preferred are silicate, dicalcium phosphate and calcium carbonate. Amounts of the abrasive will range from about 5% to about 80% by weight.

Adjunct tartar control agents, especially those containing phosphorous, may be combined with the polymers of the present invention. Inorganic phosphorous adjuncts may include any of the water-soluble pyrophosphates such as disodium pyrophosphate, dipotassium pyrophosphate and mixtures of these with tetrapotassium pyrophosphates or tetrasodium pyrophosphates. Organic phosphorous compounds that may serve as adjuncts include polyphosphonates such as disodium ethane-1-hydroxy-1, 1-diphosphonate (EHDP), methanediphosphonic acid, and 2-phosphonobutane-1,2,4-tricarboxylic acid.

For anti-caries protection, a source of fluoride ion will normally be present in the oral compositions. Fluoride sources include sodium fluoride, potassium fluoride, calcium fluoride, stannous fluoride, stannous monofluorophosphate and sodium monofluorophosphate. These sources should release anywhere from 25 to 3500 ppm of fluoride ion. The anti-caries agent will be present in an amount from about 0.05 to about 3% by weight, preferably 0.5 to 1% by weight.

Flavors that are usually present in the oral compositions are those based on oils of spearmint and peppermint. Examples of other flavoring materials include menthol, clove, wintergreen, eucalyptus and aniseed. Flavors may range in concentration from about 0.1 to 5% by weight.

Sweetening agents such as saccharin, sodium cyclamate, aspartame, sucrose and the like may be included at levels from about 0.1 to about 5% by weight.

Other additives may also be incorporated into the oral compositions including preservatives, silicones, other synthetic or natural polymers and anti-gingivitis actives.

The following examples will more fully illustrate the embodiments of this invention. All parts, percentages and proportions referred to herein and in the appended claims are by weight of the total composition unless otherwise stated.

EXAMPLE 1

Copolymers of acrylic acid and maleic acid were prepared using sodium hypophosphite to promote telomerization. In a typical reaction, sodium hypophosphite monohydrate of a desired amount was added to deionized water and the solution heated to about 90°–100° C. Maleic anhydride was added to the solution and pH adjusted to about 4. Sodium or potassium persulfate (1–10% of total monomer feed) was used to initiate the polymerization. Acrylic acid at the appropriate ratio was added periodically over a 2–4 hour time period. Polymerization was continued until substantially 100% conversion was obtained. Telomers prepared in this manner are listed in Table I.

TABLE I

| Sample | Acrylate/Maleate Ratio | Monomer/ Hypophosphite Ratio | Molecular Wt. | |
|---|---|---|---|---|
| | | | Mw | Mn |
| AM-C | 1.5:1 | 8:1 | 1200 | 700 |
| AM-D | 1.5:1 | 16:1 | 2100 | 1000 |
| AM-H | 2:1 | 32:1 | 4400 | 1700 |
| AM-F | 4:1 | 8:1 | 1400 | 600 |

The following materials listed in Table II were tested for comparative purposes.

TABLE II

| Sample | Supplier | Composition | Molecular Weight |
|---|---|---|---|
| Gantrez AN-169 | GAF | 1:1 Maleic anhydride/methyl vinyl ether | 700,000 |
| Acrysol LMW-100N | Rohm and Haas | Polyacrylic acid, Na+ salt | 10,000 |
| Acrysol A-3 | Rohm and Haas | Polyacrylic acid | 190,000 |

EXAMPLE 2 pH-Stat Assay

The procedure for the pH-Stat assay was adapted from U.S. Pat. No. 4,627,977 (Gaffar et al.). This assay is used to measure the activity of anticalculus agents in the inhibition of the transformation of amorphous calcium phosphate to HAP. The expected values are calculated by adding the delay times of the individual components.

TABLE III

| pH-Stat Assay: Agent/Agent Combinations | | | | |
|---|---|---|---|---|
| | | Delay Time (min) | | |
| Agent 1 (< MW 2500) | Agent 2 (> MW 4000) | Actual | Expected | Difference |
| AM-C (30 ppm) | — | 23.2 | 23.2 | — |
| AM-F (30 ppm) | — | 27.9 | 27.9 | — |
| — | AM-H (30 ppm) | 0.0 | 0.0 | — |
| — | LMW-100N (30 ppm) | 0.0 | 0.0 | — |
| AM-C (30 ppm) | LMW-100N (30 ppm) | 32.3 | 23.2 | +9.1 |
| AM-C (30 ppm) | AM-H (30 ppm) | 33.2 | 23.2 | +10.0 |
| AM-F (30 ppm) | AM-H (30 ppm) | 51.9 | 27.9 | +24.0 |

The results in Table III indicate that combinations of high and low molecular weight anionic polymers provide more than additive increases in activity over either of the polymer components alone.

EXAMPLE 3

Polymer/Polymer Combinations in pH-Stat Assay

When polymers not in the two desired MW ranges are combined, no additive behavior is observed. In the experiments shown below, neither of the polymers has the lower MW as required in the invention; all of the materials have MW>4000.

TABLE IV

| | | Delay Time (min) | | |
|---|---|---|---|---|
| Agent 1* | Agent 2 | Actual | Expected | Additivity |
| Acrysol A-3 | — | 0.0 | — | — |
| Acrysol LMW-100N | — | 0.0 | — | — |
| NSC 91H | — | 0.0 | — | — |
| Gantrez AN-169 | — | 0.0 | — | — |
| Acrysol LMW-100N | Gantrez AN-169 | 0.3 | 0.0 | +0.3 |
| NSC 91H | Gantrez AN-169 | 1.9 | 0.0 | +1.9 |
| Acrysol A-3 | Gantrez AN-169 | 0.0 | 0.0 | +0.0 |

*All concentrations are 30 ppm; combinations are 30 ppm each.

EXAMPLE 4

Seeded Brushite Growth

Combinations of polymers were tested in a brushite seeded crystal growth assay. To conduct the test, the desired amount of sample was placed in a centrifuge tube. Four mls of an imidazole buffer (pH 6.1) containing 10 mg of unstabilized brushite powder was placed in the tube. The sample was mixed for about 5 seconds with a vortex mixer. To the slurry was added 0.5 ml of a 53 mM calcium chloride solution and 0.5 ml of a 53 mM potassium phosphate dihydrate solution, whereupon the slurry was incubated at 37° C. on a rotary mixer for 1 hour. The sample was centrifuged and 30 μls of the supernatant were removed and analyzed for phosphorus content using the method of Chen et al. (*Anal. Chem.* 8, 1756, (1956)). A brushite sample (no agent) was typically run as a negative control. The buffer/brushite/calcium chloride/potassium phosphate dihydrate solution was analyzed for phosphorus as a positive control. Values of % Inhibition were calculated using the following relationship:

$$\% \text{ Inhibition} = \frac{\text{Sample (mM Phosphorus)} - \text{Neg. Control (mM Phosphorus)}}{\text{Pos. Control (mM Phosphorus)} - \text{Neg. Control (mM Phosphorus)}} \times 100$$

Table V lists results for individual agents and combinations of agents. Expected values were calculated by adding the actual values of the individual agents. The AM-H/Gantrez combination was included as a comparative example, as both components have molecular weights greater than 4000 and would not be considered part of this invention.

TABLE V

Polymer/Polymer Combinations in Brushite Seeded Growth Assay

| Agent 1 (Conc.) | Agent 2 (Conc.) | % Inhibition Actual | % Inhibition Expected | Difference |
|---|---|---|---|---|
| AM-C (0.5 ppm) | — | 14 | 14 | — |
| AM-H (0.5 ppm) | — | 67 | 67 | — |
| LMW-100N (0.5 ppm) | | 26 | 26 | — |
| Gantrez AN-169 (0.5 ppm) | | 8 | 8 | — |
| AM-C (0.5 ppm) | AM-H (0.5 ppm) | 99 | 81 | +18 |
| AM-C (0.5 ppm) | LMW-100N (0.5 ppm) | 95 | 40 | +55 |
| AM-C (0.5 ppm) | Gantrez (0.5 ppm) | 76 | 22 | +54 |
| AM-H (0.5 ppm) | Gantrez (0.5 ppm) | 74 | 75 | −1 |

The results indicate that polymer pairs having a combination of low and high molecular weight show more than additive behavior over the individual components. The example containing no polymer having MW below 2500 (AM-H/Gantrez) shows additivity, but not a synergistic increase in activity.

Although this invention has been described with reference to specific examples, it will be apparent to one skilled in the art that various modifications may be made thereto which fall within its scope.

What is claimed is:

1. An oral composition comprising:
   (i) a first synthetic anionic polymer having a molecular weight from greater than about 4,000 to about 1,000,000.
   (ii) a second polymer having the formula I:

$$A-\underset{\underset{R}{|}}{\overset{\overset{O}{\|}}{P}}-B \qquad (I)$$

wherein A is a random polymeric residue comprising at least one unit of structure II, $$\left[-\underset{\underset{R_1}{|}}{\overset{}{C}}H-\underset{\underset{R_2}{|}}{\overset{\overset{CO_2X}{|}}{C}}-\right]_n \qquad (II)$$

and at least one unit of structure III, different from a unit of structure II, $$\left[-\underset{\underset{R_3}{|}}{\overset{\overset{CO_2X}{|}}{C}}-\underset{\underset{R_4}{|}}{\overset{\overset{CO_2X}{|}}{C}}-\right]_m \qquad (III)$$

and B is hydrogen or a residue A; m and n are integers sufficient to provide polymer of weight averaged molecular weight ranging from about 400 to about 2500; m and n in residue A may each be the same or different from respective m and n in residue B; R is an —OX, where X is selected from the group consisting of hydrogen, alkali metal, alkaline earth metal, transition metal, ammonium, alkyl amine, alkanolammonium residues and mixtures thereof; $R_1$, $R_2$, $R_3$ and $R_4$ are hydrogen, methyl, ethyl radicals or combinations thereof, and the first synthetic anionic polycarboxylic polymer relative to the second polymer I being present in a weight ratio from about 10:1 to about 1:10 and together the first anionic polymer and second polymer providing a more than additive increase in anticalculus activity.

2. A composition according to claim 1 further comprising a fluoride source present an effective amount to reduce caries.

3. A composition according to claim 2 wherein the amount of fluoride range from about 0.05 to about 3%.

4. A composition according to claim 1 further comprising a dental abrasive present in an amount from about 5% to about 80% by weight.

5. A composition according to claim 1 wherein the second polymer has a molecular weight ranging from about 1000 to about 2300.

6. A composition according to claim 1 wherein the structure II is formed from monomers selected from the group consisting of acrylic, methacrylic, alpha-substituted acrylic, beta-carboxyalkyl acrylic acids or salts, and mixtures thereof.

7. A composition according to claim 1 wherein structure III is formed from monomers selected from the group consisting of maleic, fumaric, mesaconic, citraconic acid residues including their anhydrides or salts, and mixtures thereof.

8. A composition according to claim 1 wherein structure II relative to structure III is present in a molar ratio ranging from about 5:1 to about 1:5.

9. A composition according to claim 8 wherein said molar ratio of structures II to III ranges from about 4:1 to about 1:1.

10. A composition according to claim 1 wherein the second polymer is formed from a combination of acrylic acid or salt and maleic anhydride, its acid or salt and sodium hypophosphite.

11. A composition according to claim 10 wherein the molar ratio of total monomer to hypophosphite utilized to prepare the second polymer ranges from about 40:1 to about 1:1.

12. A composition according to claim 1 wherein the combination of first and second polymers is present in amounts ranging from about 0.1 to about 10% by weight.

13. A composition according to claim 1 wherein said first and second polymers are identical except for molecular weights.

14. A composition according to claim 1 wherein said first polymer is formed from at least one monomer selected from the group consisting of mono-carboxylic and di-carboxylic acids having 3 to 5 carbon atoms, salts, esters and anhydrides thereof, said monomer having at least one polymerizable olefinic double bond.

15. A composition according to claim 14 wherein said monomer is selected from the group consisting of acid, salt, anhydride and ester forms of acrylic, methacrylic, itaconic, fumaric and maleic acids.

16. A method of controlling dental calculus which comprises treating teeth with a composition acording to claim 1.

17. A composition according to claim 1 wherein both the first and second polymers are formed from a combination of acrylic acid, maleic anhydride and hypophosphite, the first polymer having an acrylate/maleate weight ratio of 2:1, monomer/hypophosphite weight ratio of 32:1 and molecular weight of 4,400, and the second polymer having an acrylate/maleate weight ratio ranging from 1.5:1 to 4:1 with a monomer/hypophosphite weight ratio of 8:1 and a molecular weight between 1,200 and 1,400, the weight ratio of first to second polymer being about 1:1.

18. A composition according to claim 1 wherein the first polymer is a 1:1 maleic anhydride/methyl vinyl ether of molecular weight 700,000, the second polymer is formed from a combination of acrylic acid, maleic anhydride and hypophosphite having an acrylate/maleate ratio of 1.5:1, a monomer/hypophosphite ratio of 8:1 and molecular weight of 1,200, the first and second polymers being present in a relative weight ratio of 1:1.

19. A composition according to claim 1 wherein the first polymer is a sodium polyacrylic acid of molecular weight 10,000, the second polymer is formed from a combination of acrylic acid, maleic anhydride and hypophosphite having an acrylate/maleate weight ratio of 1.5:1, a monomer/hypophosphite weight ratio of 8:1 and molecular weight of 1,200, the first and second polymers being present in a relative weight ratio of 1:1.

* * * * *